(12) United States Patent
Gesztesi et al.

(10) Patent No.: US 8,956,597 B2
(45) Date of Patent: Feb. 17, 2015

(54) OIL-IN-WATER NANOEMULSION, A COSMETIC COMPOSITION AND A COSMETIC PRODUCT COMPRISING IT, A PROCESS FOR PREPARING SAID NANOEMULSION

(75) Inventors: Jean-Luc Gesztesi, São Paulo (BR); Leandra Moraes Santos, Campinas (BR); Paulo De Tarso Hennies, São Paulo (BR); Karla Araújo Macian, São Paulo (BR)

(73) Assignee: Natura Cosmeticos S.A., Sao Paulo-Sp (BR)

( * ) Notice: Subject to any disclaimer, the term of this patent is extended or adjusted under 35 U.S.C. 154(b) by 762 days.

(21) Appl. No.: 11/577,931

(22) PCT Filed: Aug. 25, 2005

(86) PCT No.: PCT/BR2005/000222
§ 371 (c)(1),
(2), (4) Date: Sep. 13, 2007

(87) PCT Pub. No.: WO2006/045170
PCT Pub. Date: May 4, 2006

(65) Prior Publication Data
US 2009/0208541 A1    Aug. 20, 2009

(30) Foreign Application Priority Data
Oct. 26, 2004    (BR) .................................. 0404595

(51) Int. Cl.
| | | |
|---|---|---|
| A61K 8/37 | (2006.01) | |
| A61K 8/00 | (2006.01) | |
| B82Y 5/00 | (2011.01) | |
| A61K 8/06 | (2006.01) | |
| A61Q 5/00 | (2006.01) | |
| A61Q 19/00 | (2006.01) | |

(52) U.S. Cl.
CPC ... B82Y 5/00 (2013.01); A61K 8/06 (2013.01); A61K 8/062 (2013.01); A61Q 5/00 (2013.01); A61Q 19/00 (2013.01); A61K 2800/21 (2013.01); A61K 2800/413 (2013.01)
USPC ........................................... 424/63; 424/401

(58) Field of Classification Search
None
See application file for complete search history.

(56) References Cited

U.S. PATENT DOCUMENTS 6,638,519 B1 * 10/2003 Lorant .......................... 424/401
6,719,967 B1    4/2004 Brown et al.
2003/0087967 A1    5/2003 Quemin
2004/0175445 A1 *  9/2004 Hnat ............................. 424/735
2004/0208837 A1 * 10/2004 Krueger et al. ................. 424/59
2005/0048089 A1 *  3/2005 Bratescu et al. .............. 424/401
2005/0249758 A1 * 11/2005 Di Puccio Pagano ........ 424/401

FOREIGN PATENT DOCUMENTS

EP          0 191 217          8/1986
WO       WO 01/43859          6/2001

OTHER PUBLICATIONS

Emulgade MSDS Sheet Printed from website:http://www.chemiplast.hu/specik/Emulgade%20SE.pdf.*
Emulgade MSDS Sheet http://www.chemiplast.hu/specik/Emulgade%20SE.pdf.*
Lamas Beauty Archive (Apr. 2004) Retrieved online at http://web.archive.org/web/20040415011653/http:/www.lamasbeauty.com/glossary/glossary_P.htm.*
Dow Corning (Jun. 18, 2002) http://www.dowcorning.com/content/publishedlit/FORMUL_00171.pdf.*
MSDS for vegetable glycerin. Retrieved online May 2010 at: http://www.sfm.state.or.us/CR2K_SubDB/MSDS/VEGETABLE_GLYCERIN.PDF.*
Nielloud, et al., "Formulation of oil in water submicron emulsions in the dermatological field using experimental design," *Polymer International*, vol. 52, 2003; pp. 610-613.
Detweiler et al., "Antimicrobial nanoemulsions useful for decontamination of food processing plants", *Biosciences Information Service*, 2001.
Derwent Publications Ltd., London, GB; AN 1999-281621 & JP 11 090211 (Lion Corp) Apr. 6, 1999, Abstract.
Search Report and Written Opinion for PCT/BR2005/000222 dated May 24, 2006.
International Preliminary Report on Patentability dated Feb. 1, 2007.

* cited by examiner

*Primary Examiner* — Scott Long
*Assistant Examiner* — Sarah Alawadi
(74) *Attorney, Agent, or Firm* — Alston & Bird LLP

(57) ABSTRACT

The present invention relates to an oil-in-water emulsion for cosmetic use, wherein the oil particles have an average diameter ranging from 50 to 200 nm (nanometers). The nanoemulsion comprises an emulsifying system having components such as ceteareth-20, ceteareth-12, glyceryl stearate, cetearyl alcohol and cetyl palmitate. This composition imparts to the nanoemulsion an opaque coloration, besides providing to the skin inherent properties of the nanoemulsion such as better absorption of the components by the skin, imparting softness, smoothness and moisturizing for 24 hours, and may be added to products indicated for hair care. The composition of the nanoemulsion without addition of preservatives imparts a bactericidal action. The nanoemulsion is preferably used for cosmetic applications 5 for the body, face and hair in the form of milk, lotions and gels. The present invention further relates to the cosmetic compositions and cosmetic products that comprise the nanoemulsions above, as well as to a process for preparing them.

13 Claims, No Drawings

OIL-IN-WATER NANOEMULSION, A COSMETIC COMPOSITION AND A COSMETIC PRODUCT COMPRISING IT, A PROCESS FOR PREPARING SAID NANOEMULSION

This application claims the priority of Brazilian patent case No. PI0404595-5 filed on Oct. 26, 2004 which is hereby incorporated by reference.

FIELD OF THE INVENTION

The present invention relates to oil-in-water nanoemulsion used preferably for cosmetic applications for the body and face such as milk, lotions and gels and still in products indicated for hair care.

BACKGROUND OF THE INVENTION

The main function of the skin is to provide a barrier for the transport of water and substances harmful to the body. The capability of a chemical substance to penetrate the skin often depends upon the composition of the carrier. When a drug or cosmetic is applied to the skin, some situations limit the rate of cutaneous permeation: first, the release of the active from the carrier and, secondly, the penetration of the latter through the skin barrier. Active ingredients in skin-care treatment pass into the skin through the pores of the pilose follicles, the canal of the tallow glands or through corneous extract.

The corneous extract is hygroscopic, in part due to the capability of preserving water of the keratin. The skin needs at least 10% of moisturizing by weight to keep its flexibility and softness. The association of intercellular lipids with the corneocytes of the corneous extract is crucial for keeping the barrier function and the capability of linking with water.

Substances favorable to the skin are water-soluble and oil-soluble. The capability of retaining water from the corneous extract may be restored by applying lipids selected for the corneous extract and in a suitable carrier. The size of the particles and their lipophilicity are main factors in the process of penetrating through the corneous extract. The molecules go through the membrane by both passive diffusion and active transport. The transport through the skin takes place primary by passive diffusion, which is governed by Fick's law. It determines that the base rate of diffusion or transport through the membrane is proportional to the difference in concentration of active on the two sides of the membrane.

Delivery systems play an important role in the development of effective skin-care products. Anti-aging treatments stimulate the growth of the skin-treatment market. Consumers expect rapid and visible results. In order to achieve these results, many companies are relying on advanced technology. Among the "delivery" technologies, there are systems of lipids, nanoparticles, microcapsules, polymers and films. These technologies are added in a carrier such as creams, liquids, gels and patches. The key aspects of the "delivery systems" are:

increasing/improving the penetration and improving the efficacy;
controlled delivery;
separating incompatible actives;
prolonging the shelf life/decreasing the degradation of active.

Nanoparticles may be subdivided into two structure of encapsulated membrane: liposomes and nanoemulsions/nanosomes/nanotopes. Nanoemulsions differ from macroemulsions by their smaller size of oily particles, which are on the order of nanometers. Classic emulsions or macroemulsions have droplets in the size range of 1 to 20 micrometers, which impart to them the white or opaque aspect. Nanoemulsions have been characterized as being transparent or slightly translucent, depending on the particle size and on the difference in refraction index between oil phase and aqueous phase:

The nanoemulsion system may be applied in personal hygiene, pharmaceuticals, foods, household sanitary agents, agrochemicals and cosmetics.

The applicant indicates, hereinafter, the relevant documents of the prior art relating to the matter of the present invention.

Documents U.S. Pat. No. 6,274,150, BR 0000417, U.S. Pat. No. 6,464,990 and U.S. Pat. No. 6,413,527 describe a process for preparing a nanoemulsion based on phosphoric fatty acid esters. This process comprises mixing an aqueous phase and an oil phase with vigorous stirring at the temperature ranging from 10 to 80° C. to form a mixture, and homogenizing the mixture under high pressure raging from 600 bar to 1,800 bar, further carried out with a shear ranging from $2 \times 16^6$ $s^{-1}$ to $5 \times 10^8$ $s^{-1}$. Nanoemulsions present an average particle size ranging from 20 nm to 75 nm, for topical application.

On the other hand, document U.S. Pat. No. 5,994,414 describes a process for preparing an emulsion, which comprises forming a crude oil-in-water emulsion, which is subjected to homogenization under a pressure of about 900 to about 1,100 bar to obtain an average particle size of about 0.1 micron, with a maximal size of about 1 micron. The emulsion may be used in lotions for application onto the skin.

Document BR 0100335 describes oil-in-water nanoemulsions comprising particles with less than 150 nm for application in cosmetics, such as lotions and creams to be applied to the face and to the skin. In an embodiment of the invention, a process for preparing a nanoemulsion is described, which comprises mixing an oil phase and an aqueous phase by means of a homogenizer with a turbine, and then homogenizing with a homogenizer under high pressure, with 4 cycles, while keeping the temperature of the product below about 35° C.

Further, document BR 9705381 relates to the use of nanoemulsions on keratin fibers, comprising particles having an average size of less than 150 nm. These nanoemulsions are obtained by mixing an aqueous phase and an oil phase, under vigorous stirring, at a room temperature lower than 45° C., and then subjected to homogenization under high pressure.

Finally, document BR 9604724 describes an oil-in-water nanoemulsion comprising an average particle size smaller than 100 nm, intended for use on cosmetic and pharmaceutical products. The nanoemulsion may be prepared under a pressure ranging from 1,200 bar to 1,800 bar, and may present 7 cycles. The nanoemulsion may assume the form of a lotion or a gel.

All the documents cited above and still other documents of the prior art that deal with compositions and processes relating to nanoemulsion, considered less relevant for the present invention, do not disclose an oil-in-water nanoemulsion composition, be it for cosmetics or for pharmaceuticals, which exhibits an opaque coloration. Those skilled in the art know that, due to the reduced size of the oil particles dispersed in the aqueous phase, the coloration of the composition is transparent, varying, at most, to a bluish tone, as can be seen from the above-cited documents. In some of the above-listed documents, one can even see that attempts are made to achieve non-transparent nanoemulsions, by these attempts have failed in stability. In this regard, it is found that no teaching of the prior art proposes an oil-in-water composition comprising oily particles with a diameter on the order of nanometers, is stable for a period of 2 years and exhibits an opaque coloration. These characteristics and consequent advantages are comprised by the present invention and will be described hereinafter.

SUMMARY OF THE INVENTION

An objective of the present invention is to provide an oil-in-water nanoemulsion for cosmetic use, composed of an aqueous phase and an oil phase, constituted by oily particles that have an average diameter ranging from 50 to 200 nm, wherein said oily phase comprises an emulsifying system with at least ceteareth-20, ceteareth-12, glyceryl stearate, cetearyl alcohol and cetyl palmitate.

Another objective of the present invention is to provide a process for preparing the above-described nanoemulsion, which comprises the following steps:

a—adding the components of the oil phase (phase A) in an auxiliary equipment and heating up to 75° C.;

b—adding the components of the aqueous phase (phase B) in a main equipment and heating up to 75° C.;

c—adding the phase A in the main equipment and stirring at 1,500 rpm for 30 minutes, while keeping the temperature between 70° C. and 75° C.;

d—adding the cooling water (phase C) and stirring for 15 minutes at 1,500 rpm;

e—transferring the composition obtained in step d to a high-pressure homogenizing equipment provided with at least one piston. This equipment has two chambers, the first one with a pressure of 1200 bar and the second one with a pressure of 120 bar; passing the composition at least once through the equipment (completing one cycle), or for as many cycles as necessary, to obtain the average particle size between 50 and 200 nm.

Another objective of the present invention is to provide the nanoemulsion obtainable by the process described above.

A further objective of the present invention is to provide cosmetic compositions and cosmetic products that comprise the nanoemulsion characterized above.

DETAILED DESCRIPTION OF THE INVENTION

The present invention describes an oil-in-water type nanoemulsion that presents oily particles of a reduced average diameter ranging from 50 to 200 nm.

The nanoemulsion comprises an emulsifying system having components such as ceteareth-20, ceteareth-12, glyceryl stearate, cetearyl alcohol and cetyl palmitate. This composition imparts to the nanoemulsion an opaque coloration, besides providing the skin with inherent properties of the nanoemulsion, such as better absorption of the skin components, providing softness, smoothness and moisturizing.

The main examples of products that can be prepared from the nanoemulsion of the present invention are:

body moisturizing milk
face moisturizing milk
body moisturizing lotion
face moisturizing lotion
cologne
perfumed water
sanitizing water
gels
makeup remover
scalp products and
hair products.

The nanoemulsion of the present invention has a variety of advantages and characteristics desired in a cosmetic product for the skin, some of them being listed below.

1—it is stable for a period of at least two years;
2—it has an adequate texture during application, non-sticky and non-oily;
3—it is easy to spread;
4—it has an ideal time relating to the absorption and the drying of the cosmetic product on the skin;
5—it does not cause oiliness on the skin after application;
6—it has high capability of keeping the skin moisturized;
7—it does not present comedogenicity;
8—it does not present phototoxicity;
9—it does not present allergenicity;
10—it does not cause any kind of adverse reaction or lesion, be it cutaneous or ocular, in normal conditions of use;
11—it is compatible with a wide variety of actives;
12—it provides a high degree and long duration (over 24 hours) of skin moisturizing when compared with traditional emulsions, as demonstrated in the tests described herein after;
13—the nanoemulsion of the present invention has an opaque coloration, unlike nanoemulsion compositions of the prior art, by virtue of the emulsifying system used therein;
14—the nanoemulsion of the present invention may be added to skin products such as moisturizing lotions, as well as for products intended for hair care;
15—the coloration of the present nanoemulsion of the present invention has a strong commercial and marketing appeal by virtue of its visual aspect;
16—the nanoemulsion of the present invention does not comprise a thickening agent in its composition; the amounts of the components of the aqueous phase and of the oil phase and the preparation process are adequate for imparting the emulsification of the oily particles, preventing the separation of the phases and providing prolonged stability. Without a need for a thickening agent, a liquid emulsion becomes feasible in a cosmetic product;
17—the nanoemulsion of the present invention provides the skin with softness, smoothness, moisturizing, non-stickiness, high penetration and good spreadability, besides having an excellent degree of homogeneity and stability;
18—further, the object of the present invention has bactericidal action, even when it does not comprise a formulation of a bactericidal agent. The nanoparticles of the nanoemulsion of the present invention break the membranes of the bacteria, thus killing them.

Characteristics that define a nanoemulsion, as well as the components that may be used in the present invention, will now be described in greater detail.

Nanoparticles comprise oily particles dispersed in an aqueous phase, wherein the average diameter of said particles is on the order of nanometer, preferably between 50 and 200 nanometers. The coloration of the nanoemulsions had been characterized before as being transparent or slightly translucent, depending on the particle size and the difference in the refractive index between oil phase and aqueous phase. The present invention has achieved a novel and unexpected result with regard to its coloration, starting from the knowledge disclosed before.

Further, nanoemulsion are characterized as being kinetically stable systems, that is to say, they have physical stability for a longer period of time, coming close to a thermodynamically stable system, and as systems of releasing lipophilic actives, because their small particle size increases the contact area, the spreadability, the homogeneousness of the distribution and the penetration of the active into the substrate (skin/hair).

Nanoemulsion of the Present Invention

First, since it is an oil-in-water type nanoemulsion, it is evident that the amount of the oil phase is smaller than the amount of the aqueous phase. Preferably, the nanoemulsions of the present invention comprise from 2.0% to 15.0% of oil phase and 85.0% to 98.0% by weight of aqueous phase, based on the total weight of the composition of the nanoemulsion.

Further, the composition of the nanoemulsion of the present invention is constituted by an oil phase comprising an emulsifying system with at least ceteareth-20, ceteareth-12, glyceryl stearate, cetearyl alcohol and cetyl palmitate and an aqueous phase. The combination of these components brings about the opaque coloration of the cosmetic nanoemulsion described herein. The range of amount of the above-cited emulsifying system present in the oil phase is from 1.0 to 2.5% by weight, based on the total weight of the composition of the nanoemulsion.

By preference, in order to prepare the composition of the nanoemulsion in question, Emulgin B2 (ceteareth-20) and Emulgade® SE, manufactured by Cognis, are used, the latter comprising the following combination:

| | |
|---|---|
| Glyceril stearate | 40-70% |
| Ceteareth-20 | 10-20% |
| Ceteareth-12 | 5-10% |
| Cetearyl alcohol | 5-10% |
| Cetyl palmitate | 5-10% |

Silicone System

The types of silicone that may be added to the present invention act as filmogenic agents, emollients, solvents and/or skin conditioners. A few examples of silicone that may be added to the nanoemulsion of the present invention are volatile and non-volatile silicone oils such as, for example, cyclomethicone, alkyldimethicones, dimethicone-copolyols, dimeticonols, phenyl trimethicones, caprylyl trimethicones, aminofunctional silicones, phenyl modified silicones, phenyl trimethicones, alkyl modified silicones, dimethyl and diethyl polysyloxane, $C_1$-$C_{30}$ mixed alkyl polysiloxane, α-methyl-ω-methoxypolymethylsiloxane, polyoxydimethylsililene, polydimethyl silicone oil and combinations thereof, or silicone elastomers such as cyclomethicone crosspolymer and dimethicone, vinyl dimethicone crosspolymer and dimethicone, dimethicone crosspolymer and dimethicone and cyclopentasiloxane crosspolymer and dimethicone.

In the preferred embodiments of the present invention, phenyl trimethicone is added in the oil phase in an amount ranging from 1.0% to 5.0% by weight, based on the total weight of the composition of the nanoemulsion.

Emollient

The function of the emollients in cosmetic compositions is to add or replace lipids and natural oils to the skin.

As emollients to be added to the nanoemulsion of the present invention, one may use conventional lipids such as, for example, oils, waxes, lipids and other water-soluble components and polar lipids that are modified lipids so as to increase their solubility in water by esterification of a lipid to a hydrophilic unit such as, for example, hydroxyl, carbonyl groups, among others. Some compounds that may be used as emollients are natural oils such as essential oils and plant derivatives, esters, silicone oils, polyunsaturated fatty acids, lanoline and derivatives thereof. Some natural oils that may be used are derived from damson, passion fruit, Para-nut, carap nut, cupuassu, sesame, soybean, peanut, coconut, olive, cocoa, almond, avocado, carnauba, cotton seed, rice bran, peach stone, mango stone, jojoba, macadamia, coffee, grape seed, pumpkin seed, among others, and mixtures thereof.

In addition, a number of natural compounds may be used, as for example, microcrystalline wax, camauba wax, Shea butter, bee-wax, ozokeri wax, among others and mixtures of waxes and/or oils.

In the preferred embodiments of the present invention, an oil from the Brazilian biodiversity (cupuassu butter/carap oil/Para-nut oil/passion-fruit oil) is used as emollient in the oil phase in an amount ranging from 0.1% to 10.0% by weight, based on the total weigh of the composition of the nanoemulsion.

Moisturizing Agent

The moisturizing agent promotes the retention of water in the skin, that is to say, it is capable of supplying water to the skin and also preventing the loss of water from the skin. The wetting agent further helps in increasing the efficacy of the emollient, reduces skin peeling and improves the sensorial properties of the skin (softness, smoothness).

A few examples of wetting agents that may be added to the nanoemusion of the present invention are: glycerin, glycereth-26, PET-4 dilaurate, polyhydroxyl alcohols, alkylene polyols and derivatives thereof, glycerol, ethoxylated glycerol, propoxylated glycerol, sorbitol, hydroxypropyl sorbitol, among others, lactic acid and lactate salts, diols and $C_3$-$C_6$ triols, Aloe vera extract in any form, as for example, in the form of a gel, sugars, and starches and derivatives thereof, as for example, alkoxylated glucose, hyaluronic acid glycolic acid, lactic acid, glycolic acid and salicylic acid, pantenol and urea.

In the preferred embodiments, vegetable glycerin or glycereth-26 are used in an amount ranging from 3.0% to 10.0% by weight, and biosaccharide gum 1 in an amount ranging from 1.0% to 5.0% by weight, based on the total weight of the composition of the nanoemulsion.

Fragrance

It is optional to add to the compositions of this type perfume or fragrance selected from a variety of possible substances. The amount of fragrance in the oil phase to be added to the nanoemulsion of the present invention preferably ranges, if present, from about 0.2% to about 6.0% by weight, based on the total weight of the composition of the nanoemulsion.

Carrier

Water is the base of several possibilities of cosmetic compositions prepared from the base cosmetic composition already described, acting as the carrier for the other components. The aqueous phase of the nanoemulsion of the present invention comprises preferably demineralized or distilled water at an adequate percentage (q.s.p.) to achieve 100% of the formula, based on the total weight of the composition of the nanoemulsion.

Other Optional Components

In order to provide the nanoemulsion of the present invention with some desirable characteristic that has not yet been achieved with the already cited components, one may add optional components that are compatible with the properties thereof. Some of these compounds that may be added to the composition are as follows:

active principles: they may be either lipophilic or hydrophilic, for example, seaweeds, a combination of palmitoyl hydroxypropyl trimonium aminopectin, glycerin crosspolymer, lecithin and grape-seed extract, bisabolol (anti-inflammatory active), D-pantenol (conditioning active), tocopherol (vitamin E), retinol (vitamin A), ascorbic acid (vitamin C), erocalcipherol (vitamin D)

and sunscreen commonly added to compositions of products for topical or hair use;

bacteriostatics, bactericides or antimicrobials, as for example, Irgasan DP300;

dyes;

chelating agent as ethylenediaminotetraacetic acid (EDTA) and salts thereof;

pH adjusting agent, like triethanolamine;

preservative like DMDM hydantoin;

plant extract: chamomile, rosemary, thyme, calendula, carrot extract, common juniper extract, gentian extract, cucumber extract;

skin conditioning agent;

lipophilic substances antioxidant agent, like butyl hydroxytoluene (BHT), butyl hydroxyanisol (BHA); and other components commercially accepted, which are compatible with the base composition.

EXAMPLES OF COMPOSITION

The following examples are preferably variations of the nanoemulsion of the present invention, and should not be interpreted as limitations thereof. In this regard, it should be understood that the scope of the present invention embraces other possible variations, being limited only by the contents of the accompanying claims, which include the possible equivalents.

| Component | Mass amount (%) |
|---|---|
| Cupuassu butter | 1.00 |
| Ceteareth-20 | 0.36 |
| Phenyl trimethicone | 2.50 |
| BHT | 0.05 |
| BHA | 0.05 |
| Emulgade SE ® | 2.14 |
| Demineralized water | 16.00 |
| Dissodic EDTA | 0.20 |
| Vegetable glycerin | 5.00 |
| Biosaccharide gum-1 | 3.00 |
| Demineralized water | Qsp 100 |
| Ess. Confort 404 | 0.50 |
| Orange solution K 7011 | 0.15 |
| Blue solution | 0.02 |
| Red solution 0.2% | 0.02 |
| Yellow solution | 0.25 |
| triethanolamine | 0.03 |
| DMDM Hytantoin/IPBC | 0.05 |

Example 1

Cupuassu Butter Milk

Observation: example 1 illustrated above may also contain carap-nut oil and Pará nut to replace cupuassu butter. These compositions were used to carry out the tests described later.

| Component | Function | Phase |
|---|---|---|
| Cupuassu butter | Emollient | A |
| Ceteareth-20 | Emulsifier | A |
| Phenyl trimethicone | Silicone | A |
| BHT | Antioxidant agent | A |
| BHA | Antioxidant agent | A |
| Emulgade SE ® | Emulsifying agent | A |
| Demineralized water | Carrier | B |
| Dissodic EDTA | Chelating agent | B |
| Vegetable glycerin | Moisturizing agent | B |
| Bisaccharidic gum 1 | Moisturizing agent | B |
| Demineralized water | Carrier | C |
| Ess. Confort 404 | Fragrance | D |
| Orange solution K 7011 | Dye | E |
| Blue solution | Dye | E |
| Red solution 0.2% | Dye | E |
| Yellow solution | Dye | E |
| Triethanolamine | pH adjusting agent | F |
| DMDM Hydantoin/IPBC | Preservative | G |

Example 2

Passionfruit Milk

| Component | Mass amount (%) |
|---|---|
| Passionfluit oil | 5.00 |
| Ceteareth-20 | 0.20 |
| Phenyl trimethicone | 3.00 |
| BHT | 0.05 |
| BHA | 0.05 |
| Emulgade SE ® | 1.80 |
| Demineralized water | 20.00 |
| Disodic EDTA | 0.20 |
| Biosaccharidic gum - 1 | 2.00 |
| Vegetable glycerin | 8.00 |
| Demineralized water | Qsp 100 |
| Despert Essence | 0.50 |
| Yellow solution | 0.30 |
| Triethanolamine | 0.03 |
| DMDM Hydantoin/IPBC | 0.05 |

Example 3

Passionfruit Milk

| Component | Mass amount (%) |
|---|---|
| Passionfluit oil | 8.00 |
| Ceteareth-20 | 0.40 |
| Phenyl trimethicone | 2.00 |
| BHT | 0.05 |
| BHA | 0.05 |
| Emulgade SE ® | 2.00 |
| Demineralized water | 20.00 |
| Disodic EDTA | 0.20 |
| Biosaccharidic gum - 1 | 2.00 |
| Vegetable glycerin | 10.00 |
| Demineralized water | Qsp 100 |
| Despert Essence | 0.50 |
| Yellow solution | 0.30 |
| Triethanolamine | 0.03 |
| DMDM Hydantoin/IPBC | 0.05 |

| Component | Function | Phase |
|---|---|---|
| Passionfluit oil | Emollient | A |
| Ceteareth-20 | Emulsifying agent | A |
| Phenyl trimethicone | Emollient | A |
| BHT | Antioxidant agent | A |
| BHA | Antioxidant agent | A |
| Emulgade SE ® | Emulsifier | A |
| Water | Carrier | B |
| Disodic EDTA | Chelating agent | B |
| Biosaccharidic gum | Moisturizing agent | B |
| Vegetable glycerin | Moisturizing agent | B |
| Demineralized water | Carrier | C |

-continued

| Despert Essence | Fragrance | D |
| Yellow solution | Dye | D |
| Triethanolamine | pH adjuster | F |
| DMDM Hydantoin/IPBC | Preservative | G |

Process of Preparing the Nanoemulsion

The nanoemulsion of the present invention may be prepared by the process described below, the phases cited therein being as follows:

| Phase A | At lest one type of oil |
| | Emulgin B2 |
| | Emulgade ® SE |
| Phase B | Water |
| Phase C | Cooling water |

Phase A may comprise any oil commonly used in oil-in-water emulsion compositions known and further butter(s) or mixtures of oil(s) and butter(s).

Step I—Preparation of the Emulsion a—Mixing the components of the emulsifying system (phase A) in an auxiliary equipment and heat up to 75° C.;

b—adding water (Phase B) to a main equipment and stirring at 1500 rpm for 30 minutes, while keeping the temperature between 70° C.-75° C.; and c—adding cooling water (Phase C) and stirring for 15 minutes at 1500 rpm.

Optionally, one may further perform the substep e, as follows:

e—adding components such as fragrance, preservatives, dyes, hydrophilic actives, among others to the composition of step d.

Said stirring should preferably occur in rotor-stator homogenizers.

Step II—Preparation of the Nanoemulsion from the Prepared Emulsion a—transferring the composition obtained in Step I to a high-pressure equipment having preferably 1 to 3 pistons; this equipment has two chambers, the first one with pressure of 1200 bar and the second one with pressure of 120 bar;

i.—the nanoemulsion of the present invention is automatically transferred from the first chamber that is under a pressure of 1200 bar to the second chamber that is under a pressure of 120 bar, completing the cycle;

b—in order to obtain the average particle size of 50 to 200 nm, repeat, if necessary, the above substep, totalizing three cycles, at most.

Alternatively, one may use a different number of cycles, if different particle sizes are desired.

The passage of the emulsion through this difference in pressure (depressurization) causes explosion of the oil drops and collision thereof against the walls of the second chamber. Then the particles have a diameter on the order of nanometers. In order to obtain an average particle size of about 50 to 200 nm, one should pass the emulsion 1 or 3 consecutive times through this equipment.

This is a more simple process than those already known, since only one passage through the above-described equipment is required. Techniques for preparing nanoemulsions of the prior art of the present usually recommend the use of more cycles and do not express the need to depressurize (1200 bar down to 120 bar) to reduce the particle size down to the order or nanometers.

Examples of a Process for Preparing Nanoemulsion

To exemplify the process, the composition of nanoemulsion described in example 1 above will be used.

| Phase A | Emulgin B2 |
| | Emulgade ® SE |
| | Cupuassu butter |
| | Phenyl trimethicone |
| | BHT |
| | BHA |
| Phase B | Demineralized water |
| | Disodic EDTA |
| | Vegetable glycerin |
| | Diosaccharidic gum |
| Phase C | Demineralized cooling water |
| Phase D | Confort Essence 404 |
| Phase E | Orange solution K 7011 |
| | Blue solution |
| | Red solution 0.2% |
| | Yellow solution |
| Phase F | Triethanolamine |
| Phase G | DMDM Hydantoin/IPBC |

Step I a—adding the components of phase A in an auxiliary equipment and heating up to 75° C.;

b—adding the components of phase B in a main equipment and heating up to 75° C.;

c—adding the phase A in the main equipment under stirring of about 1500 rpm for 30 minutes, while keeping the temperature between 70° C. and 75° C.;

d—adding cooling water (phase C) and stirring for 15 minutes at 1500 rpm;

e—adding the phase D and stirring for 5 minutes;

f—adding the phase E and stirring for 5 minutes;

g—adding the phase F and stirring for 5 minutes;

h—adding the phase G and stirring for 5 minutes;

Step II a—inserting the emulsion obtained in step (h) into the high-pressure equipment and the product will pass through two chambers: the first chamber being under a pressure of 1200 bar and the second chamber being under a pressure of 120 bar, totalizing a cycle to obtain the average particle size between 50 and 200 nm.

Tests of the Oil-in-Water Nanoemulsion of the Present Invention

Three sets of tests were carried out, comprising clinical studies and consumer/user evaluation tests.

First set: the composition defined in EXAMPLE 1, containing Pará-nut oil;

Second set: the composition defined in EXAMPLE 1, containing carap oil:

Third set: the composition defined in EXAMPLE 1, containing cupuassu butter.

Below, some achieved results are reported.

1—Clinical Studies a—Mono-Blind, Randomized, Controlled, Clinical Study of the Potential of Irritability, Sensitization, Phototoxicity and Cutaneous Photoallergy This study has the function of evaluating adverse reactions that may be caused with application of the nanoemulsion to the skin. By adverse reactions one understands any signal or symptom triggered by a topical product used correctly. As examples of adverse reactions, one may cite contact eczematous dermatitis, urticaria, acne and stains.

The irritation potential of a product depends on a number of variables: the components of the composition, the concentration of each of the components, absorption thereof by the skin, the amount applied onto the skin, the state in which the skin at the time of application, the manner and frequency of application of the product onto the skin and the inherent cumulative effect of the product.

Patch test is the main tool used in diagnosing a reaction caused by a cosmetic and in researching allergenicity. In the research of allergenicity, the following clinical tests are involved: primary and accumulated dermal irritability, cutaneous sensitization, phototoxicity and photoallergy. These consist in repeated applications of the product onto the skin and have the function of detecting possible irritations or induction of sensitization. It is indicated to carry out use tests after approval of the product in patch tests. With the use tests one may evaluate, in addition to allergenicity, sensorial characteristics of the products, that is, their performance.

In order to carry out the allergenicity tests for each set, 130 volunteers were selected, of both sexes (123 women and 7 men), of all races, with age ranging from 18 to 65, excluding individuals who had dermatological diseases, lesions or nerves on the back and pregnant or breast-feeding women.

In order to carry out this study, the following material was used: hypoallergenic adhesive card for patch test with duly identified filter paper discs of 1.0 $cm^2$, semipermeable hypoallergenic adhesive plaster for occlusion, saline solution and samples of the cosmetic composition. 0.05 g of the cosmetic composition was applied to each area of 1 $cm^2$ of the filter paper disc, and the saline solution was applied onto the control disc. These discs were fixed onto the back of the volunteers with adhesive plaster. The following clinical researches were also carried out.

I—Research on Primary Irritability

The test method used was the patch test. The place of application of the tests was the back of the volunteers, duly protected. The patch test was removed by the researches after 48 hours of contact with the skin, and the reactions were written down, 30 minutes after removal.

II—Research on Accumulated Irritability

The sample was always applied in the same region, on the back, duly protected. The applications were all made on the same day, the patch test remaining 72 hours in the end of the week, for 4 consecutive weeks, in a total of 20 applications. The sample was reapplied onto the skin always on the same spot and the reactions were written down. After 20 consecutive applications, a rest period of 10 followed, when no patch was applied. After this rest interval, a simple patch of sample was applied onto the back of the volunteers in a virgin area, that is to say, a place where no patch had been applied. The test was removed by the researchers after 48 hours of contact with the skin and the reactions were written 30 minutes after removal.

III—Research on Sensitization

The sample was always applied in the same region on the back, duly protected. The applications were made 3 times per week for 3 consecutive weeks, on alternate days, resulting in a total of 9 applications. The patch test was removed by the researches 24 hours after application thereof. After a series of 9 consecutive applications, a rest period of 20 days followed, when no patch was applied. Then, a simple patch of the sample was applied onto the back of the volunteers, in the virgin area. The patch test was removed by the researchers after 48 hours of contact with the skin and the reactions were written down 30 minutes after removal.

IV—Research on Photoallergy

By phototoxicity one understands an increase in cutaneous reactivity to ultraviolet light, without immunological base, and by photoallergy one understands the increase in cutaneous reactivity to ultraviolet light with immunological base.

The test was carried out as follows: the nanoemulsion was applied onto the back of the volunteers at a concentration of 0.05 $g/cm^2$ in an always protected region. The applications were made twice a week for 3 weeks resulting in a total of 6 applications. The patch test was removed by the researchers 24 hours after application, the area being immediately evaluated and irradiated with an A and B ultraviolet lamp. The non-irradiated back areas and the eyes were duly protected from light incidence. The sample was always reapplied on the same place. After 6 consecutive applications and irradiations, a rest period of 10 days followed, when no patch and no irradiation were made. The tests were removed by the researchers after 24 hours of application. After removal, the test areas were irradiated with an UVA lamp. The volunteers were instructed to protect the irradiated area against sunlight. Evaluations were made 24, 48 and 72 hours after the last irradiation and written down on a form for this purpose.

V—Research on Phototoxicity

The nanoemulsion was applied onto the back of the volunteers at a concentration of 0.05 g/cm in an always protected region. The application was made only once. The patch test was removed by the researchers 24 hours after application, the area being immediately evaluated and irradiated with an A ultraviolet lamp. The non-irradiated areas of the back and the eyes were duly protected against light incidence. Then, a patch was applied onto the back of the volunteers with saline solution, in the virgin area, and irradiated. The volunteers were instructed to protect the irradiated area against sunlight. Evaluations were made 24, 48 and 72 hours after the last irradiation and written down on a form for this purpose.

Result: the tests carried out evidenced the absence of cutaneous sensitizations, and no process of irritation, sensitization or phototoxicity or photoallergy was identified during the study in the three sets.

b—A Clinical, Open Study of Cutaneous Tolerability in Real Conditions of Use

The objective of this test is to determine the prevalence of adverse reactions in real conditions of use of the products that comprise the nanoemulsion of the present invention, used in the three sets of test.

First set: for this test, 27 female volunteers were selected, with age ranging from 18 to 53 years.

Second set: for this test, 25 female volunteers were selected, with age ranging from 18 to 64 years.

Third set for this test 29 female volunteers were selected, with age ranging fro 20 to 57 years.

Volunteers having a history of generalized or localized dermatological diseases, pregnancy and breast-feeding were excluded.

The volunteers were guided to use the product for 3 weeks, being supervised by dermatologists.

Result: in real conditions of use, no volunteer presented any kind of adverse reaction with respect to the use of the products in the three sets.

c—A Clinical, Moonblind, Randomized, Controlled Study of the Skin-Moisturizing Power The objective of this test is to evaluate the skin-moisturizing power of the products that comprise the nanoemulsion of the present invention, used in the three sets of test.

First set: for this test, 18 female volunteers were selected, with age ranging from 18 to 60 years.

Second set: for this test, 20 female volunteers were selected with age ranging from 18 to 60 years.

Third set: for this test, 20 female volunteers were selected, with age ranging from 18 to 60 years.

Volunteers with generalized or localized dermatological diseases, pregnancy or breast-feeding were excluded.

c.1) Corneometry

It was carried out by using the apparatus Corneometer CM 820, Courage+Khazaka electronic GMbH of a measuring probe.

The readings were made by applying the probe to the test area, with the pressure permitted by the spring. The measurement area was of 49 mm². 20 measurements were made in each area.

The reading indicated the degree of moisture of the skin surface based in variations of electric capacity. The scale of the apparatus is arbitrary, the highest reading values indicating greatest moisturizing.

First Step:
- in each set, the volunteers remained at rest in a air-conditioned room, with temperature of 20±2° C. and relative humidity of 50±5% for 30 minutes;
- two symmetrical, 25 cm² areas of the front region of the legs having a randomized distribution were demarcated for application of the product, and one area was kept as control area.
- The electric capacity of these areas was determined through the arithmetic means of 20 measurements.

Second Step:
- In each set, the tested product was applied in the amount of 50 µl in the demarcated region of each volunteer.
- The electric capacity of the regions was measured after 1, 2, 3, 5, and 8 hours, while keeping the volunteers at rest in an air-conditioned room.

Analysis of the Results:

Descriptive statistics were calculated and graphs and lines were built for the measurements of the treatment as time went by. The comparative analysis of the products and controls was carried out by means of the paired test 1. The level of significance considered in the analysis was of 5%.

Result: in all the sets, no volunteer presented any kind of adverse reaction in the area of application of the product. The products brought about an increase in the skin moisturizing, evidenced by the increase in corneometry, at the level of significance of 5%, in all the times evaluated with respect to the control.

d—A Clinical, Non-Blind, Randomized, Controlled Study of the Skin Moisturizing

This study aims at evaluating the skin moisturizing power of the nanoemulsion of the present invention.

First set: for this test, 20 female volunteers were selected, with age ranging from 28 to 58 years.

Second set: for this test, 20 female volunteers were selected, with age ranging from 28 to 58 years.

Third set: for this test, 20 female volunteers were selected, with age ranging from 28 to 58 years.

Volunteers with generalized or localized dermatological disease, pregnancy and breast-feeding were excluded.

Further, two additional sets in comparative tests were carried out.

Fourth set: for this test, 20 female volunteers were selected, with age ranging from 28 to 58 years. A composition in cream form (ordinary oil-in-water emulsion) with carap oil was used.

Fifth set: for this test, 20 female volunteers were selected, with age ranging from 28 to 58 years. A composition in cream form (ordinary oil-in-water emulsion) with cupuassu oil was used.

For this study, the following were used: a Corneometer CM 820, which measures the water contents in the skin, specifying the degree of moisturizing of the skin surface. The product was applied to determined areas with 25 cm² of the legs. A third area is kept without product (control). The measurements of the corneometer area carried out in the beginning of the test and after application of the product onto the skin in determined periods of time of 24 hours. All these measurements are effected in a specific room (moisturizing room), where the temperature and the moisture are monitored (maximal temperature of 22° C. and maximal relative humidity of 55%). With the measurements, one determines the electric capacity of these regions.

Then, one uses software designed for this type of study, in order to determine, in a graphic and numerical manner, the moisturizing power of each of the nanoemulsion compositions of the 5 sets described above.

Result: according to this test, no volunteer presented any kind of adverse reaction in the areas of application of the products.

With respect to the first three sets, when one compares the productless area and the test areas, in which the cosmetic compositions are applied, the skin presents different moisturizing levels. The moisturizing is evidenced by the increase in the corneometry. One then concludes that the compositions of examples 1 to 3 provide moisturizing to the skin for at least 24 hours.

On the other hand, the results referring to the fourth and the fifth sets show that these creams do not provide a difference in moisturizing to the skin.

Therefore, one can see that exhibit significantly greater moisturizing potential/power than the tested creams that comprise traditional oil-in-water emulsion (average particle size between 4 and 12 microns), both nanoemulsion and oil-in-water emulsion comprising the same concentration of wetting agent (glycerin 5%).

e—Test for Efficacy of Preservatives—Challenge Test

The objective of this test is to evaluate the efficacy of cosmetic preparations, in this case, nanoemulsion of the present invention, for their preserving property, even without comprising a preservative in their composition. Compositions of example 1 with Para-nut oil, cupuassu butter and carap oil were tested. The test for efficacy of preservatives consists in intentionally contaminating the sample with specific microorganisms and evaluating this charge at defined intervals of time.

The following equipment and products were used: graduated sterilized pipettes of 5.0 and 1.0 ml or micropipettes, sterilized sticks and spatulas, sterilized flasks with screwed caps, sterilized Petri plates, sterilized platinum strap or loops, incubation stove at 35° C., incubation stove at 25° C., autoclave, laminar flow, sterilizing and drying stove, container for disposal of pipettes, sterilized wooden sticks, sterilized gauzes, rubber pearl, diluent broth, saline solution at 0.85%, tryptic soy agar (TSA), sabourad dextrose agar (SAB), agar nutrient, agar malt, ttc solution at 1% (2,3,5 triphenyl tetrazolium chloride), disinfecting solution (example, alcohol at 70%), isopropyl myristrate.

The following microorganisms were used:

| Type | Microorganism |
| --- | --- |
| Gram positives | *Staphylococcus aureus* ATTCC 6538 |
| | *Streptococcus mutans* (factory contaminant) |
| Fermented gram negatives | *Escherichia coli* ATTCC 8739 |
| Non-fermented gram netatives | *Pseudomonas aeruginosa* ATTC 9027 |
| | *Burkholderia cepacia* ATTC 25608 |
| | *Burkholderia cepacia* (20011) - internal (in house) contaminant Vitaplant - 2003 |

The stock bacterium cultures were chopped in tubes containing "Tryptic Soy" Agar or Nutrient Agar slants and incubated at 35° C. for 24 hours. The residues (bulks) containing the analyzed samples were identified.

One found the suitability of the diluent medium used by the analysis method: Evaluation of the Inactivation of the Preservative System.

1—Preparation of the Inoculum 1.1—Bacterium Cultures chopping each of the bacterium cultures in tubes containing TSA or Nutrient Agar slant with the aid of sterilized loop;

incubating the tubes (35+/−2)° C. for 18-24 hours;

suspending, with the aid of a sterilized loop, each microorganism in test tube containing 9 ml of saline solution (0.85%), identified with the name of the microorganism so as to obtain about $10^8$ UFC/ml (turbidity similar to tube No. 1 of the MacFarland Scale);

stirring property the suspension so as to eliminate the presence of lumps.

1.2—Assembling the Pool of Bacteria assembling a pool of gram-positive bacteria and one of gram-negative bacteria;

transferring the whole contents of the tubes containing the gram-positive bacteria into a single sterilized flask with a cap identifying it as gram-positive pool;

transferring the whole contents of the tubes containing the gram-negative bacteria into a single sterilized flask with a cap identifying it as gram-negative pool.

2—Bacterium Inoculation identifying the flask containing 40 g of the sample received from the laboratory, previously weighed, as gram-positive and gram-negative;

simultaneously inoculating 0.4 ml of the gram-positive suspension in the product and in sterilized flask containing 40 ml of saline solution 0.85% (control);

repeating the same procedure with the gram-negative suspension;

homogenizing the residue containing the product contaminated with the inoculum by using a sterilized glass stick;

the inoculated saline solution will serve as a control for obtaining the initial number of microorganism in the zero-contact time, and for evaluating the feasibility of the microorganisms after 7 and 28 days from the incubation; diluting the inoculated saline solution down to the dilution of 10-6, by using 9 ml of sterile saline solution at 0.85% per flask; pipetting 1 ml of each dilution to sterile Petri plates;

adding about 20 ml of Tryptic Soy Agar culture medium plus the TTC 1% solution, previously cooled to 45° C. (for each 400 ml of medium, add 1.5 ml of each TTC solution);

homogenizing with rotary 8-shaped movements;

incubating the inverted Petri plates at 35+/−° C. for 48 hours;

carry out the counting of the number of colonies formed; multiplying the results obtained by the dilution factor; preferably counting the plates with count between 25 and 250 colonies.

3—Analysis of Bacteria carry out the counting of bacteria 24 hours, 7, 14, 21 and 28 days after inoculation;

weighing 1 gram of sample in 9 ml of diluent broth;

make the necessary dilutions ($10^{-1}$ to $12^{-6}$), by using 9 ml of sterile saline solution at 0.85%; pipetting 1 ml of each dilution to sterile Petri plates;

adding about 20 ml of Tryptic Soy Agar culture medium plus TTC solution, previously cooled to 45° C.;

homogenizing with rotary 8-shaped movements;

incubating the plates at 35° C. for 48 hours;

making the counting of the number of colonies formed; multiplying the results obtained by the dilution factor; preferably counting the plates with count between 25 and 250 colonies;

registering the results.

4—Control of Feasibility of the Microorganisms carrying out the counting of bacteria of the inoculated saline solution (control) in the initial time, 7 and 28 days after incubation;

registering the results achieved.

5. Criteria for Approval 5.1—Cosmetic Products reducing 99.9% of the initial charge, or three logarithmic cycles, in the interval of time equal to 7 days, for bacteria.

5.2—Cosmetic Products for Areas of the Eyes and Infants reducing more than 99.9% of the initial charge, or three logarithmic cycles, in the interval of time equal to 7 days, followed by continuous reduction down to <10 UFC/g at the end of the period of test for bacteria;

reducing 90.00% of the initial charge, or one logarithmic cycle, in the interval of time equal to 7 days, followed by continuous reduction down to <UFC/g at the end of the period of test for fungi.

Result: the nanoemulsion compositions of the present invention without any preservative agent like DMDM Hydantoin/IPBC exhibited a significant result of preservation when tested with all the species of bacteria mentioned before.

f—Analysis of the Particle Size Ion Products on the Mastersizer Equipment

The objective of this analysis is to determine the distribution of particle sizes in products through laser ray diffraction, by using the equipment Mastersizer Plus MAF 5001—Malvern.

The particles dispersed in the dispersing liquid are transported through an optical cell, onto which a laser beam having a wavelength equal to 630 nm falls. Upon passing through the optical cell, the particles cause the light to spread in several angles. The values of these angles are inversely proportional to the particle sizes. The spread light is detected by sensors positioned below the angles, and the analysis of the diffraction pattern enables the calculation of the particle size of the sample.

The following equipment and products were used: apron, safety glasses, gloves, equipment Mastersizer Plus MAF 5001—Malvern, paper lenses (or soft absorbent paper), 600 ml or 15 ml beaker, automatic micropipette (100 ul to 1000 ul), ethyl alcohol at 96% and lauryl ether sodium sulfate.

The procedure of the analysis is as follows:

adjusting the conditions of equipment, analysis and presentation, documenting the analysis, adding the dispersing liquid in the dispersion unit, actuating the pump, making the alignment, measuring the which background, adding the sample and making the measurement, using the data corresponding to the sample to be analyzed;

calculating the average values;

Result: the particles of the traditional oil-in-water emulsions analyzed exhibited a diameter ranging from 4 to 12 microns; these emulsions were also analyzed for their moisturizing power (24 hours), compared with the nanoemulsions of the present invention.

g—Evaluation of the Particle Size by the Operation of the Equipment Zetasizer 3000 (Malvern).

The objective of this evaluation is to normalize the procedures of operation of the equipment Zetasizer 3000 (Malvern) for carrying out the analysis of particle size.

The following equipment, materials and reactants were used: equipment Zetasizer 3000 Malvern, microcomputer, automatic micropipette, graduated (2 ml) glass pipette, rubber pipetter, paper handkerchief, disposable acrylic or glass tubettes, with a cap, lauryl ether sodium sulfate and ethanol at 96%.

The evaluation was carried out according to the following procedure:

selecting the most suitable dispersant (indications on manual MANO149) and filtering it through 0.2 µm membrane;

depending on the type of the dispersant, using the appropriate tubette;

disposable acrylic tubette for an aqueous dispersant; or
glass tubette for an organic or siliconed dispersant;

checking the conditions of the dispersant: place 2 ml of the filtered dispersant in the tubette, closing it and positioning it in the equipment;

preparing the sample;

removing the tubette from the equipment (containing the 2 ml of dispersant);

adding an aliquot of the sample in the tubette with the dispersant (writing down the amount of sample employed);

closing the tubette, harmonizing the liquid gently by manual stirring (avoid the use of ultrasound for emulsions) and replacing it in the equipment;

carrying out the measurements in the computer.

The experimental conditions are: ultrafiltered water (MilliQ), volume of the sample: V=1 ul, I. R.=1.331 (water); I. R.=1.59 (oil phase).

Result: the particles of the compositions analyzed exhibited an average diameter ranging from 50 to 200 nm (nanometers).

The invention claimed is:

1. An oil-in-water nanoemulsion for cosmetic use as a cosmetic product for skin care, scalp care and hair care, composed of an aqueous phase and an oil phase constituted by oily particles that have an average diameter ranging from 50 to 200 nm, characterized in that the amount of oil phase ranges from 2.0% to 15.0% by weight, based on the total weight of the nanoemulsion composition, said oil phase comprises an emulsifying system with at least ceteareth-20, ceteareth-12, glyceryl stearate, cetearyl alcohol and cetyl palmitate, wherein the amount of the emulsifying system present in the oil phase ranges from 1.0% to 2.5% by weight, based on the total weight of the nanoemulsion composition and in that the nanoemulsion is prepared by a process comprising the following steps:

Step I:
a—adding the components of the oily phase being at least ceteareth-20, ceteareth-12, glyceryl stearate, cetearyl alcohol and cetyl palmitate (phase A) in an auxiliary equipment and heating up to 75° C.;
b—adding the components of the aqueous phase which comprises at least water (phase B) in a main equipment and heating up to 75° C.;
c—adding the phase A in the main equipment under stirring of about 1500 rpm for 30 minutes, while keeping the temperature between 70° C. and 75° C.;
d—adding cooling water (phase C) and stirring for 15 minutes at 1500 rpm;

Step II:
a—transferring the composition obtained in Step I to a high pressure equipment comprising at least one piston and two chambers, the first chamber being under a pressure of 1200 bar and the second chamber being under a pressure of 120 bar (depressurization).

2. A nanoemulsion according to claim 1, characterized in that the amount of glyceryl stearate present in the emulsifying system ranges from 40.0% to 70.0% by weight, based on the total weight of the composition of the emulsifying system.

3. A nanoemulsion according to claim 1, characterized in that the amount of ceteareth-20 present in the emulsifying system ranges from 10.0% to 20.0% by weight, based on the total weight of the composition of the emulsifying system.

4. A nanoemulsion according to claim 1, characterized in that the amount of ceteareth-12 present in the emulsifying system ranges from 5.0% to 10.0% by weight, based on the total weight of the composition of the emulsifying system.

5. A nanoemulsion according to claim 1, characterized in that the amount of cetearyl alcohol present in the emulsifying system ranges from 5.0% to 10.0% by weight, based on the total weight of the composition of the emulsifying system.

6. A nanoemulsion according to claim 1, characterized in that the amount of cetyl palmitate present in the emulsifying system ranges from 5.0% to 10.0% by weight, based on the total weight of the composition of the emulsifying system.

7. A nanoemulsion according to claim 1, characterized in that the Step I comprises an addition substep:
e—adding additional components to the composition of step d selected from the group constituted by: fragrance, preservative, dye hydrophilic actives, and combinations thereof.

8. A nanoemulsion according to claim 1, characterized in that the Step II comprises an additional substep:
b—passing the composition through the high pressure equipment until the desired particle diameter has been achieved.

9. A cosmetic composition characterized by comprising the nanoemulsion as defined in claim 1.

10. A nanoemulsion according to claim 1, further comprising phenyl trimethicone in an amount ranging from 1 to 5 weight percent based on the total weight of the nanoemulsion.

11. A nanoemulsion according to claim 1, further comprising vegetable glycerin or glycereth-26 in an amount ranging from 3 to 10 weight percent based on the total weight of the nanoemulsion, and biosaccharide gum in an amount ranging from 1 to 5 weight percent based on the total weight of the nanoemulsion.

12. A nanoemulsion according to claim 1, wherein the nanoemulsion includes an emollient selected from the group consisting of cupuassu butter, carap oil, para-nut oil, and passion fruit oil, and wherein the emollient is present in an amount ranging from 0.1 to 10 weight percent based on the total weight of the nanoemulsion.

13. A nanoemulsion according to claim 1, further comprising phenyl trimethicone and passion fruit oil, wherein the amount of phenyl trimethicone is from 1 to 5 weight percent based on the total weight of the nanoemulsion, and passion fruit oil, wherein the amount of passion fruit ranges from 0.1 to 10 weight %, based on the total weight of the nanoemulsion.

* * * * *